United States Patent [19]
Miller et al.

[11] Patent Number: 5,411,528
[45] Date of Patent: May 2, 1995

[54] ELECTRICALLY PROGRAMMABLE POLARITY CONNECTOR FOR AN IMPLANTABLE BODY TISSUE STIMULATOR

[75] Inventors: Leslie S. Miller, Saugus; John R. Helland, Santa Clarita, both of Calif.

[73] Assignee: Pacesetter, Inc., Sylmar, Calif.

[21] Appl. No.: 979,083

[22] Filed: Nov. 19, 1992

[51] Int. Cl.$^6$ .............................................. A61N 1/08
[52] U.S. Cl. ...................................... 607/5; 307/127; 607/37; 607/38
[58] Field of Search ........ 128/419 D, 419 P, 419 PG; 307/113, 127, 139; 607/5, 7, 9, 13, 37, 38, 148

[56] References Cited

U.S. PATENT DOCUMENTS

| | | | |
|---|---|---|---|
| Re. 31,990 | 9/1985 | Sluetz et al. | 128/419 P |
| 3,924,641 | 12/1975 | Weiss | 128/419 PG |
| 4,686,380 | 8/1987 | Angott | 307/113 |
| 4,800,883 | 1/1989 | Winstrom | 128/419 D |
| 4,998,531 | 3/1991 | Bocchi et al. | 128/419 D |
| 5,044,367 | 9/1991 | Endres et al. | 128/419 D |
| 5,083,562 | 1/1992 | de Coriolis et al. | 128/419 D |
| 5,111,816 | 5/1992 | Pless et al. | 128/419 PG |
| 5,182,466 | 1/1993 | Ohkubo | 307/127 |
| 5,199,429 | 4/1993 | Kroll et al. | 607/5 |
| 5,216,303 | 6/1993 | Lu | 307/113 |

FOREIGN PATENT DOCUMENTS 0326290  8/1989  European Pat. Off. ................ 607/5

Primary Examiner—William E. Kamm
Assistant Examiner—Marianne Parker
Attorney, Agent, or Firm—Leslie S. Miller; Samuel M. Katz; Malcolm J. Romano

[57] ABSTRACT

A programmable output connector of an implantable cardioverter-defibrillator (ICD), or similar implantable medical device, allows each of a multiplicity of output terminals to be selectively connected to either a positive or a negative output bus of the ICD. The positive and negative output buses of the ICD, in turn, are switched to an output capacitor, or equivalent output circuit, of the ICD. An electrical charge stored on the output capacitor, or otherwise generated by the output circuit, is presented to the multiplicity of output terminals in accordance with a programmed polarity. The programmed polarity causes a selected one or group of the multiplicity of output terminals to be connected to the positive output bus, and a selected other or group of the multiplicity of output terminals to be connected to the negative output bus. Respective electrodes designed for contacting cardiac tissue may then be electrically connected to each one of the multiplicity of output terminals. An electrical charge available on the positive and negative output buses may then be transferred to the body tissue as an electrical shock or stimulus through the electrodes in accordance with the programmed polarity.

22 Claims, 4 Drawing Sheets

ELECTRICALLY PROGRAMMABLE POLARITY CONNECTOR FOR AN IMPLANTABLE BODY TISSUE STIMULATOR

FIELD OF THE INVENTION

The present invention relates to implantable medical devices and methods, and more particularly, to an implantable cardioverter-defibrillator (ICD) that utilizes an output connector coupled to a multiplicity of implantable leads and/or electrodes. More particularly, the invention relates to a programmable output connector for use with an ICD, or similar implantable medical device, that allows the polarity of multiple electrodes connected thereto to be selectively changed using noninvasive programming techniques.

BACKGROUND OF THE INVENTION

Implantable cardioverter-defibrillators (ICD's) are medical devices that deliver high energy electrical stimulation pulses to cardiac tissue in an attempt to terminate sensed life-threatening cardiac arrhythmias, such as ventricular fibrillation (very fast, chaotic heart rhythms), or slow intrinsic cardiac rates or asystole (a non-beating heart). Hereafter, all such cardiac conditions are referred to generically as a "cardiac arrhythmia." As such, ICD's include sensing circuits for sensing cardiac activity; logic and control circuits for analyzing the sensed cardiac activity to determine if it is representative of a dangerous cardiac arrhythmia, and for controlling the ICD to respond accordingly; and output circuits for generating and delivering high energy stimuli designed to terminate the sensed dangerous cardiac arrhythmia.

One type of ICD, designed for use with an implantable pacemaker, is shown in U.S. Pat. No. 4,989,602 (Sholder et al.), which patent is incorporated herein by reference. The ICD disclosed in the '602 patent advantageously allows the programmable sensing circuits of the pacemaker to be used to help control the ICD. Many other types of ICD's are known and practiced in the art. See, e.g., Cannon, "Implantable Cardioverter-Defibrillator: The Promise and Perils of an Evolving Technology," PACE, Vol. 15, pp. 1–4 (January 1992).

The output circuits of an ICD typically include a charging circuit and one or more output capacitors. The charging circuit is coupled to a low voltage battery, and builds up a high energy charge on the output capacitor over time (0.5–4 seconds). Once the output capacitor has been charged to a prescribed level, which may be from 5 to 40 joules, and once a determination is made by the logic and control circuits of the ICD that a high energy stimulus (commonly referred to as a "defibrillation pulse," a "cardioversion pulse" or simply a "shocking pulse") is needed, the output capacitor is selectively coupled between suitable output terminals of the ICD to appropriate defibrillation leads. The defibrillation leads are essentially insulated electrical conductors that electrically connect the output terminals of the ICD to suitable defibrillation electrodes, judiciously positioned on, in or near a patient's heart, at a distal end of the defibrillation leads. Thus, placing the charge on the output terminals of the ICD effectively places the charge between the defibrillation electrodes, where it discharges as a shocking pulse through the body tissue found between the electrodes.

The effectiveness of the ICD shocking pulse at terminating a given sensed cardiac arrhythmia is determined by numerous factors, such as the energy of the stimulus, the positioning of the electrodes, the design of the electrode, and the type of electrodes. Further, it has been learned in recent years that the effectiveness of a given shocking pulse can be markedly improved by delivering the shocking pulse through a multiplicity of electrodes, each of which is judiciously positioned on, in or near, the cardiac tissue.

When a multiplicity of electrodes are used, it has also been discovered that the polarity of the multiplicity of electrodes relative to each other at the time the discharge is delivered can also influence the effectiveness of the discharge in terminating the sensed cardiac arrhythmia for a given patient. Thus, it is well known to implant a multiplicity of defibrillation leads, e.g., three or more, and position their respective electrodes around and/or in the heart. During the implantation process, such leads are then manually coupled to the positive and negative output terminals of the ICD, and a test discharge is delivered so that its effect can be observed. For example, if three leads are used, two may be connected to the positive output terminal of the ICD, and the other is connected to the negative output terminal. Disadvantageously, it is difficult to predict in advance which of the multiplicity of leads should be coupled to the positive output terminal, and which should be coupled to the negative output terminal. The implanting physician must thus experiment during the implantation process as to what would be the best polarity configuration for a given patient; which experimentation is highly undesirable, particularly when it must be performed by manually connecting different ones of the defibrillation leads together in order to test a given polarity configuration. Hence, there is a need in the art for an ICD that can be quickly and safely implanted in a patient and coupled to a multiplicity of defibrillation leads and electrodes, while still preserving the ability to change the polarity of the electrodes.

Further, it is not uncommon for a patient to exhibit different physiological characteristics at the time of implant than are exhibited after implant. Thus, what might be an optimum polarity configuration for the defibrillation electrodes at the time of implant, may not be optimum a few days, weeks, or even months after implant. Further, as a patient ages, takes certain medications or is exposed to differing environments that create different types of physiological stress, the optimum polarity configuration for the defibrillation leads may likewise change. Thus, the optimum polarity configuration for delivering a shocking pulse for a given patient can very likely change over time. Disadvantageously, existing ICD devices, once implanted, provide no way to alter the polarity of the output electrodes short of explanting the ICD and reversing or switching the leads to achieve appropriate polarity of the lead. Hence, what is needed is an ICD that can be noninvasively programmed as required, in order to selectively alter its output polarity configuration.

SUMMARY OF THE INVENTION

The present invention addresses the above and other needs by providing a programmable output connector for use with an implantable cardioverter-defibrillator (ICD), or similar implantable medical device, designed to deliver high energy electrical shocking pulses to cardiac tissue through a multiplicity of defibrillation leads and electrodes. The output connector has a multiplicity of output terminals to which the multiplicity of defibrillation leads and electrodes may be respectively connected. A programmable switching network within the output connector selectively connects each of the output terminals to either a positive output bus or a negative output bus of the ICD, with at least one output terminal being connected to the positive output bus, and at least another of the output terminals being connected to the negative output bus. The switching network includes a first array of switches that selectively connects each output terminal to either the positive output bus or the negative output bus as controlled by polarity control signals. The polarity control signals, in turn, are generated by the ICD control logic in response to programmed control parameters selected by a physician using conventional noninvasive programming techniques.

In one embodiment of the invention, the positive and negative output buses of the ICD are coupled to an output capacitor, or equivalent output circuit, of the ICD through a discharge switch. When the discharge switch is closed, the electrical charge stored on the output capacitor, or otherwise generated by the output circuit, is presented to the multiplicity of output terminals in accordance with the polarity selected by the programmable switching network. The electrical charge available on the positive and negative output bus is then transferred to the cardiac tissue as a shocking pulse through the defibrillation leads and electrodes in accordance with the programmed polarity.

In a further embodiment of the invention, the switching network further includes a second array of switches that selectively connects the positive and negative output buses to a sense circuit within the ICD in accordance with a programmed polarity. The sense circuit has first and second inputs, and the second array of switches thus selectively connects the positive output bus to either the first or second input of the sense circuit, and connects the negative output bus to the other of the first or second input, as controlled by appropriate programmable control signals.

The present invention, in accordance with one aspect thereof, may thus be characterized as an implantable cardioverter-defibrillator (ICD). Such ICD includes a multiplicity of output terminals to which a multiplicity of defibrillation leads and electrodes may be detachably connected. The ICD also includes a switch network that selectively connects each of the multiplicity of output terminals to a positive or negative output bus. An output circuit of the ICD develops and stores an electrical charge and presents such stored charge to the positive and negative output buses. The ICD further includes: sensing means for sensing cardiac activity; control means for determining if the sensed cardiac activity indicates the need for a shocking pulse and for controlling the output circuit and switch network so as to discharge the shocking pulse through the switch network and multiplicity of output terminals in accordance with a programmed polarity; and telemetry means for noninvasively programming the control means with a set of control parameters that define the polarity of the multiplicity of output terminals.

In accordance with another aspect, the invention may be characterized as a programmable polarity output connector for use with an ICD. The ICD has an output capacitor, having a positive capacitor terminal and a negative capacitor terminal, that may be selectively charged to a prescribed energy level in anticipation of transferring the energy from the output capacitor to cardiac tissue of a patient. The programmable polarity output connector includes at least a first, a second, and a third output terminal. Programmable coupling means are also included for programmably coupling a selected one of the first, second or third output terminal to the positive capacitor terminal, and a selected other of the first, second or third output terminals to the negative capacitor terminal. Thus, using the programmable coupling means, the first, second and third output terminals may be programmed to assume a desired polarity with respect to the positive and negative capacitor terminals, with at least one of the first, second or third output terminals being coupled to the positive capacitor terminal, and with at least another of the first, second or third output terminals being coupled to the negative capacitor terminal. Hence, the programmable polarity output connector permits the output capacitor to be discharged through selected ones of the at least first, second and third output terminals while the output terminals assume a selected polarity relative to the positive and negative capacitor terminals.

In accordance with yet another aspect of the invention, a method is provided of programmably altering the polarity of a multiplicity of output terminals of an ICD. Such method includes: (a) connecting each of the multiplicity of output terminals to a corresponding multiplicity of switch pairs, each of the multiplicity of switch pairs including a positive switch that switchably connects the corresponding output terminal to a positive voltage bus, and a negative switch that switchably connects the corresponding output terminal to a negative voltage bus; (b) coupling the operation of each of the switch pairs so that it is not possible to short the positive voltage bus to the negative voltage bus through the given switch pair; (c) further coupling the operation of the switch pairs so that at least the positive switch of one switch pair connects its corresponding output terminal to the positive voltage bus at the same time that the negative switch of another switch pair connects its corresponding output terminal to the negative voltage bus; and (d) programmably setting the positive and negative switches of each of the multiplicity of switch pairs so that the corresponding output terminal is connected to one of the positive or negative voltage buses. Thus, in this manner, the output terminals are configured to assume a desired polarity relative to each other and the positive and negative voltage buses, with at least one of the multiplicity of output terminals being coupled to the positive voltage bus, and another of the multiplicity of output terminals being coupled to the negative voltage bus.

It is thus a feature of the present invention to provide an ICD that can be quickly and safely implanted in a patient and coupled to a multiplicity of defibrillation leads and electrodes, while still preserving the ability to change the polarity of the electrodes.

It is another feature of the invention to provide an ICD that can be noninvasively programmed as required in order to selectively alter its output polarity configuration.

It is a further feature of the invention to provide a programmable output connector for use with an implantable medical device, such as an ICD, that selectively configures the output terminals of the device to a desired polarity.

It is yet another feature of the invention to provide a programmable polarity output connector for a cardioverter-defibrillator (ICD) that allows a multiplicity of defibrillation leads and electrodes to be connected to the ICD in accordance with a programmed polarity, without having to physically alter the placement of the defibrillation leads.

It is another feature of the invention to provide a method of programmably altering the polarity of a multiplicity of output terminals of an ICD.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
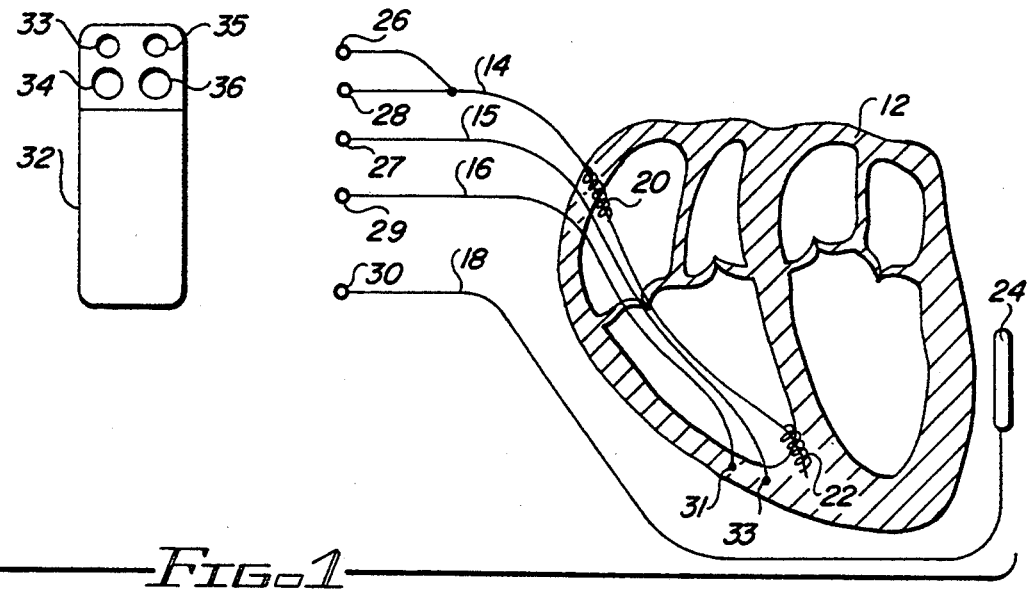
FIG. 1 illustrates the common technique used at present to determine the optimum output polarity of an ICD that interfaces with a multiplicity of electrodes coupled to a patient's heart.

In FIG. 1, an ICD of the currently known art is shown schematically, illustrating one method in which the polarity of a multiplicity of defibrillation leads and electrodes connected to the ICD is determined. As shown in FIG. 1, a patient's heart 12 is shown having three shocking electrodes 20, 22 and 24 in contact therewith. The electrode 20 is a helically wound coil at a proximal end of a transvenously placed lead 14 such that the electrode 20 is placed above, on, or below the superior vena cava (SVC). The electrode 22 is also a helically wound coil at the distal end of the lead 14 and is positioned in the ventricle. Proximal ends 26 and 28 of the lead 14 facilitate making electrical contact with electrodes 20 and 22, respectively. The electrode 24 is typically a subcutaneous electrode placed under the skin near the heart 12. A proximal end 30 on lead 18 facilitates making electrical contact with the subcutaneous electrode 24. Typically, two unipolar pacing leads 15 and 16 are used to provide pacing and sensing in the ventricle. The unipolar leads may be transvenous (active or passive) leads or myocardial leads, and are configured to function as a bipolar pacing/sensing electrode system. The pacing leads 15 and 16 each have a proximal end 27 and 29 coupled to electrodes 33 and 31, respectively.

The ICD's of the prior art, however, have heretofore typically been limited to include only two output terminals 34 and 36, at least insofar as delivery of a high energy shocking pulse is concerned. In FIG. 1, the ICD 32 is shown to include four output terminals 33, 34, 35 and 36. Typically, the output terminals 33 and 35 were used for the two unipolar pacing leads 15 and 16. Alternately, the output terminals 33 and 35 may be used for separate atrial and ventricular pacing leads (not shown). In either case, only two output terminals (34 and 36) were available for delivery of a shocking pulse. Furthermore, the output terminals 34 and 36 would be hardwired to one of a positive (+) or a negative (−) terminals of the ICD's output circuitry.

Some physicians have shown that a multiple electrode system is more effective at defibrillating the heart since the discharge current can be made to flow through more and/or different cardiac tissue. Thus, for example, if both the electrodes 20 and 22 are configured as the cathode (−) with the electrode 24 configured as the anode (+), then the discharge current may flow through a larger area of cardiac tissue than using only electrodes 22 and 24. Alternately, a physician may elect to use electrode 22 as the negative (−) cathode, with electrodes 20 and 24 as the positive (+) anode. As another example, some physicians are implanting three patch electrodes (e.g., two electrodes on the left ventricle and one on the right ventricle). There is also much dispute over which polarity is most effective for such patch electrodes. In reality, each patient is different and must be independently evaluated.

When a multiplicity of leads/electrodes and tissue sites are possible to carry the shocking pulse to the heart, and only a pair of output terminals are provided by the ICD to which the terminals are to be connected, a problem arises in knowing which leads should be connected to which output terminal to provide the most effective therapy. At present, such determination is typically made manually, in the operating room (O.R.) by performing limited experimentation during the implantation process. When two or more electrodes (e.g., electrodes 20 and 24) are to be connected to the same ICD output terminal, then the physician performing the implantation must somehow physically secure the proximal ends 26 and 30 to the single output terminal 34. Such dual connection is difficult to achieve in the operating room absent special "Y" adapters that allow two leads to be inserted into a single connector slot. However, such dual connection may be achieved, for example, by pulling the proximal end off of one of the two leads so as to expose the flexible conductor therein and physically wrapping the exposed physical conductor around the proximal end of the other lead, and then inserting the proximal end with conductor wrapped therearound into the output connector so as to make physical and electrical contact with the output terminal 34. Needless to say, such procedure, of physically pulling off the proximal end of one lead so that it can be manually wrapped around the proximal end of the other lead is not recommended.

In some ICD's currently under clinical investigation, the output terminal 33 is configured to accept a bipolar pacing lead, and output terminals 34, 35 and 36 are used with an three-electrode system, such as the three electrodes 20, 22 and 24 shown in FIG. 1. However, each of the output terminals 34, 35 and 36 are hardwired for a particular polarity. For example, output terminal 35 may be hardwired as the positive (+) anode, with output terminals 34 and 36 both configured as the negative (−) cathode. Again, the ICD 32 has a fixed output polarity. Post-implant, the attending physician would not be able to change the electrode polarity absent another operation to expose the ICD and physically reconfigure the leads.

Thus, it has been the practice in the prior art to manually select an optimum polarity configuration for the multiplicity of electrodes by performing appropriate tests during the implantation process, and manually connecting the leads together so as to provide, at least for the present, an optimum polarity configuration. Unfortunately, as also mentioned previously, an optimum polarity configuration for a particular patient may not be a constant, but may change over time. There is thus a need in the art for an ICD device that can selectively alter its output terminal configuration using noninvasive programming techniques, as required, in order to best meet the needs of the patient.

Figure 2:
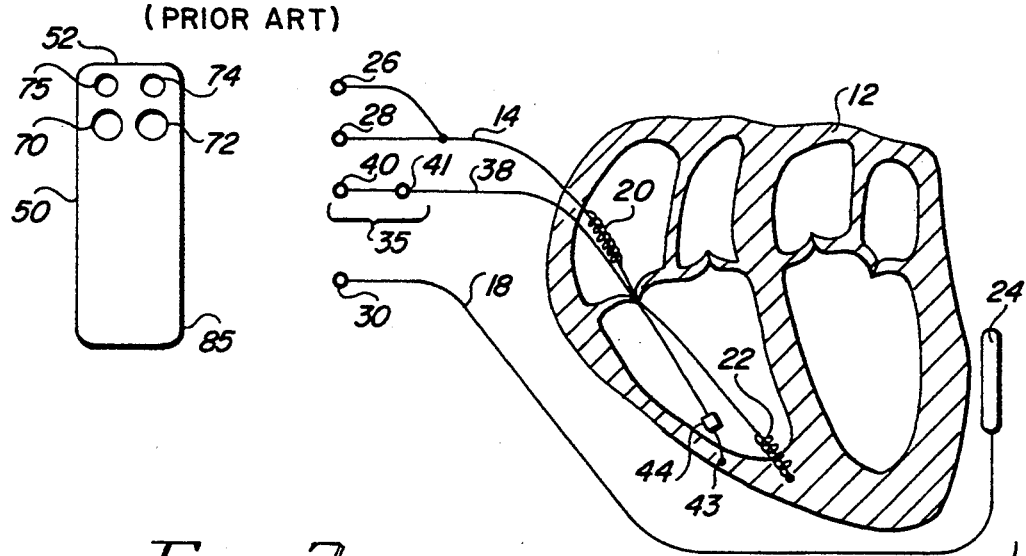
FIG. 2 shows a simplified schematic diagram of an implantable cardioverter-defibrillator (ICD) having a programmable output connector made in accordance with the present invention.

There is shown, in FIG. 2, an ICD 50 having a programmable output connector made in accordance with the present invention. In the preferred embodiment, a lead 38 having an in-line bipolar proximal end 35 is detachably secured, for example, to a bipolar output terminal 75 of the ICD 50. The lead 38 includes a tip and a ring electrode 43 and 44 coupled to proximal terminals 40 and 41, respectively. (To provide A-V synchrony, one or two electrodes in the atrium could be added, in which case the output connector 75 would be a tripolar or a quadrapolar connector, respectively, as is known in the art. Alternately, A-V synchrony could be achieved by using an additional conventional pacing lead in combination with an additional output terminal.) Each of the shocking electrodes 20, 22 and 24 would be detachably secured to one of the remaining unipolar output terminals 70, 72 and 74 of the ICD 50 through proximal ends 26, 28 and 30, respectively.

As is known in the art, the distal electrodes 20, 22 and 24 may be selectively positioned within or near the heart of the patient in conventional manner. For example, the electrode 22 may be positioned inside of the right ventricle using conventional transvenous lead placement techniques commonly used for pacemaker leads. The electrodes 22 and 24 may be positioned on or near the outside of the heart using one or more of the techniques described in U.S. Pat. Nos. 4,946,457 (Elliott); 4,991,603 (Cohen et al.); or 4,998,975 (Cohen et al.); or variations thereof, which patents are incorporated herein by reference. The defibrillation leads and electrodes may be constructed as is also known in the art. See, e.g., U.S. Pat. No. 4,774,952 (Smits), also incorporated herein by reference.

It is to be emphasized that the present invention is not limited to an ICD that interfaces with only three defibrillation leads and electrodes as shown in FIG. 2. Rather, three leads/electrodes are shown only as an example. One of the advantages of the present invention is that it may be used with a multiplicity of leads/electrodes, from three to six, or more, each of which leads-/electrodes may be judiciously positioned in, on or near the patient's heart using any known, or yet-to-be-developed implantation technique. Further, the specific lead/electrode configurations used with the present invention may be any of the type that are presently known and widely used, such as active or passive fixation transvenous leads with endocardial electrodes, epicardial patch electrodes, and the like; or the lead/electrode configurations may be of a yet-to-be-developed type. Indeed, the present invention has a wide applicability and may be used with a wide variety of lead and electrode types and placement techniques.

Figure 3:
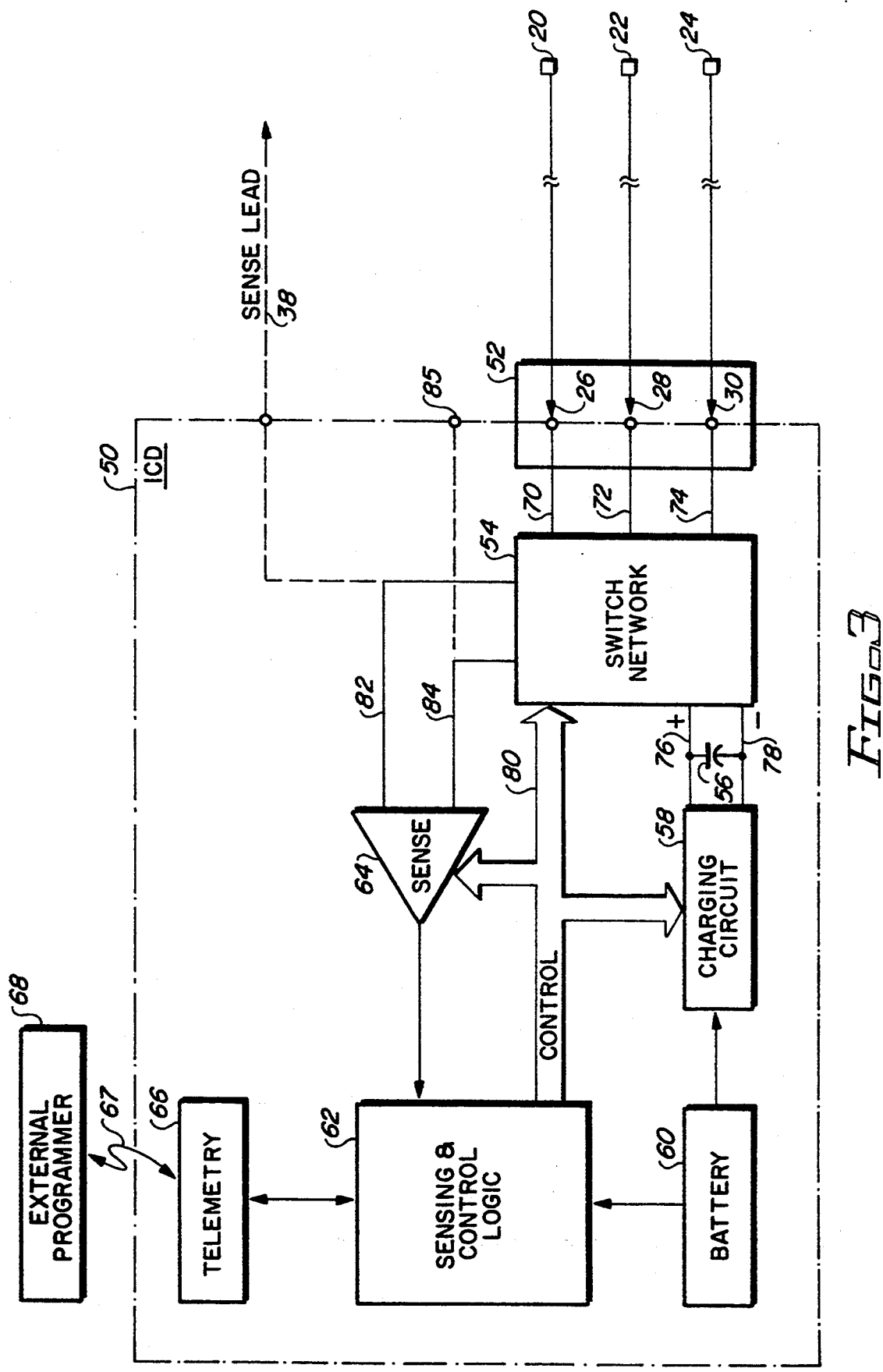
FIG. 3 shows a simplified functional block diagram of an implantable cardioverter-defibrillator (ICD) having a programmable output connector made in accordance with the present invention.

As shown schematically in FIG. 3, the proximal ends 26, 28 and 30 of the multiplicity of shocking electrodes 20, 22 and 24, respectively, are detachably secured into a suitable connector block 52 of the ICD. Such connector block serves the function of providing a secure physical and electrical connection between the proximal electrodes 26, 28 and 30 and the corresponding output terminals 70, 72 and 74 of the ICD. The particular design of the connector block 52 is not critical to the present invention. Indeed, any suitable design may be employed as is known and described in the art, using whatever specifications are required so as to provide a proper physical and electrical interface with the proximal electrode of the particular lead that is used.

The output terminals 70, 72 and 74 of the ICD 50 are outputs of a switch network 54. The switch network 54 comprises the heart of the present invention and is described more fully below in conjunction with FIGS. 4–7. Basically, however, the function of the output switch network 54 is to switchably connect a positive output bus 76 or a negative output bus 78 to one of the output terminals 70, 72 or 74, as controlled by appropriate control signals available on a control bus 80. The switch network 54 may also provide, in some embodiments, appropriate sense lines 82 and 84, on which the activity of the heart may be monitored by a sense amplifier 64 as sensed through selected ones of the multiplicity of electrodes 20, 22 and 24. Such sensing by the sense amplifier 64 is important to the operation of the ICD 50 because the ICD needs to determine when a cardiac arrhythmia occurs that warrants the generation and delivery of a shocking pulse. In other embodiments of the invention, however, it is noted that the sense lines 82 and 84 may sense cardiac activity through a separate sense lead/electrode, such as the pacing lead 38 and tip electrode 43, using either the ring electrode 44 or an ICD case electrode 85 as the return.

Still referring to FIG. 3, it is seen that the positive output bus 76 and the negative output bus 78 are connected to an output capacitor 56. While only a single output capacitor 56 is shown in FIG. 3, it is to be understood that a plurality of output capacitors, in an appropriate configuration, may likewise be used. It is the function of the output capacitor 56 to store an electrical charge of a prescribed energy. Such energy represents the energy that is delivered to the cardiac tissue through the shocking pulse. The energy is charged on the output capacitor 56 by a suitable charging circuit 58. The charging circuit derives its energy from a battery 60. Typically, the battery 60 is of a relatively low voltage (for example, a lithium-silver vanadium-oxide battery, Model No. 8830, manufactured by Wilson Greatbatch, has an open circuit voltage between 3.1–3.3 volts). The charging circuit 58, using appropriate control signals from the control bus 80, pumps up this voltage, using conventional voltage multiplying techniques, to a suitable discharge voltage, which may be as high as 700 volts or higher.

Controlling the operation of the ICD 50 is appropriate sensing and control logic 62. The sensing and control logic 62, as its name implies, monitors the output of the sense amplifier 64 and determines when a shocking pulse is required. It then generates the appropriate control signals, available on control bus 80, for causing the charging circuit 58 to begin charging the output capacitor 56 to a prescribed level. When the charge on the output capacitor 56 has reached the prescribed level, the sensing and control logic 62 further issues appropriate control signals that cause such charge to be discharged through the switch network 54 and through the output terminals 70, 72 and 74 (and hence to the electrodes 20, 22 and 24).

As with all implantable medical devices, the ICD 50 further includes a telemetry circuit 66 that allows selected control parameters associated with the sensing and control logic 62 to be programmably altered. The telemetry circuit 66 establishes a telemetry link 67 with an external programmer 68 when a programmed change in one or more of the operating parameters of the sensing and control logic 62 is desired. Such control parameters may define, for example, the energy to be included in the shocking pulse; the type of cardiac arrhythmia that must be sensed before a shocking pulse is generated; the amplitude of the signals that must be sensed on the sense lines 82 and 84 before such signals are considered as valid cardiac signals, timing intervals associated with the operation of the ICD, and the like.

Advantageously, the telemetry circuit 66 and the external programmer 68 may be of conventional design, of the type that are commonly used to monitor and control implantable cardiac pacemakers. See, e.g., U.S. Pat. Nos. 4,809,697 (Causey et al.) and 4,944,299 (Silvian), incorporated herein by reference. The design of the telemetry circuit 66 and external programmer 68 is thus not critical for purposes of the present invention so long as such design allows control parameters used within the sensing and control logic 62 to be noninvasively monitored and updated (programmed).

A key aspect of the present invention is to store within the sensing and control logic 62 a set of polarity control parameters that defines the output polarity configuration of the switch network 54. Such set of polarity control parameters is made available to the switch network 54 over the control bus 80 and causes the switch network 54 to assume a prescribed polarity configuration at its output terminals 70, 72 and 74. Advantageously, such output polarity configuration can thus be readily changed, as needed, by simply reprogramming the set of polarity control parameters using conventional programming techniques available through the telemetry circuit 66 and the external programmer 68.

For purposes of the present invention, the sensing and control logic 62 need not be significantly different than similar circuitry used in other ICD's known in the art. It may, for example, be realized with dedicated logic circuits, with a microprocessor, or a combination of processor-type circuits and dedicated logic circuits. The sensing and control logic 62 should have sufficient programmable memory therein to store the set of polarity control parameters used to define the desired output polarity of the output terminals of the ICD. As indicated below, a single bit for each output terminal is usually sufficient. Thus, for example, a set of polarity control parameters may be considered as a multibit polarity "word," with each bit defining the polarity of a respective output terminal. Appropriate memory access circuitry must also be utilized to allow such polarity word, once programmed into the sensing and control logic 62, to be placed on the control bus 80 for use by the switch network 54. Further, either within the sensing and control logic 62 or within the switch network 54, appropriate drive circuits, interface circuits, and the like, may be used as required to convert a particular polarity control parameter found on the control bus 80 to a signal that effectuates a desired result, e.g., a signal that closes or opens a given switch. All such circuits are conventional in the art, and will not be described herein.

Figure 4:
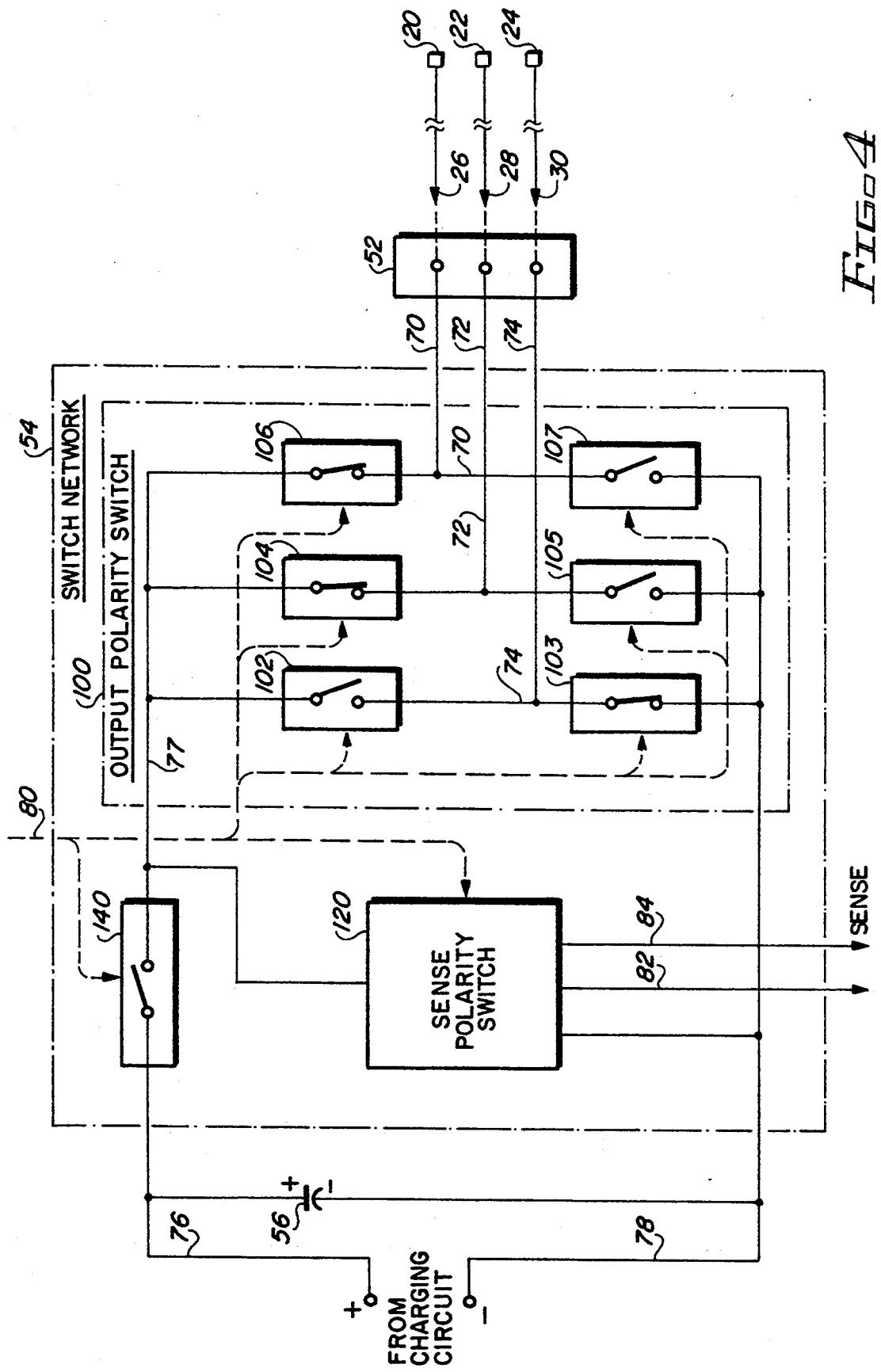
FIG. 4 is a schematic functional diagram of an output polarity switch used within the switch network of FIG. 3.

In FIG. 4, a more detailed description of the switch network 54 is presented. The switch network 54 forms the heart of the present invention. As seen in FIG. 4, the switch network 54 includes at least an output polarity switch 100. Most embodiments of the switch network 54 will also include a discharge switch 140. Some embodiments of the switch network may further include a sense polarity switch 120. However, neither the discharge switch 140 nor the sense polarity switch 120 are required by the invention, as the functions performed by these elements may either be omitted, performed by the output polarity switch 100 or performed by other conventional circuits of the ICD.

As seen in FIG. 4, the positive output bus 76 couples the positive side or terminal of the output capacitor 56 into the output polarity switch 100 through the discharge switch 140. (It is to be understood that the discharge switch 140, or equivalent, could also be placed so as to couple the negative side or terminal of the output capacitor 56 into the output polarity switch 100.) The positive output bus 76, after it passes through the discharge switch 140, is referred to as the switched bus 77.

The output polarity switch 100 includes a multiplicity of switch pairs 102–103, 104–105 and 106–107 that respectively connect the output terminals 70, 72 or 74 to the switched bus 77 and a negative output bus 78. That is, a first switch 102 of the switch pair 102–103 connects the output terminal 74 to the switched bus 77; and a second switch 103 of the switch pair 102–103 connects the output terminal 74 to the negative output bus 78. In similar fashion, the switches 104 and 106 respectively connect the output terminals 72 and 70 to the switched bus 77; and the switches 105 and 107 respectively connect the output terminals 72 and 70 to the negative output bus 78.

Appropriate means are used to prevent the two switches of each switch pair from being closed at the same time. Thus, it is not possible for both switch 102 and switch 103 of the switch pair 102–103 to connect the output terminal 74 to both the switched bus 77 and the negative output bus 78 at the same time. In a similar manner, it is not possible for the switches 104 and 105 of the switch pair 104–105 or the switches 106 and 107 of the switch pair 106–107, to be closed at the same time. In this manner, it is not possible to short the switched bus 77 to the negative output bus 78 through any of the switch pairs.

Further, appropriate controls are implemented, preferably in the sensing and control logic 62 or in the external programmer 68, to ensure that at least one of the switch pairs connects its corresponding output terminal to the switched bus 77, and at least another of the switched pairs connects its corresponding output terminal to the negative output bus 78. In this manner, at least one of the output terminals will always be positive, and another of the output terminals will always be negative, thereby assuring that the shocking pulse will have both a forward and return path from the cardiac tissue. In other words, except for diagnostic and test purposes, it is not possible for the output polarity switch to configure its output terminals to be all positive or all negative. Rather, during use, at least one of the output terminals 70, 72 or 74 must be positive and at least one must be negative.

Figure 5:
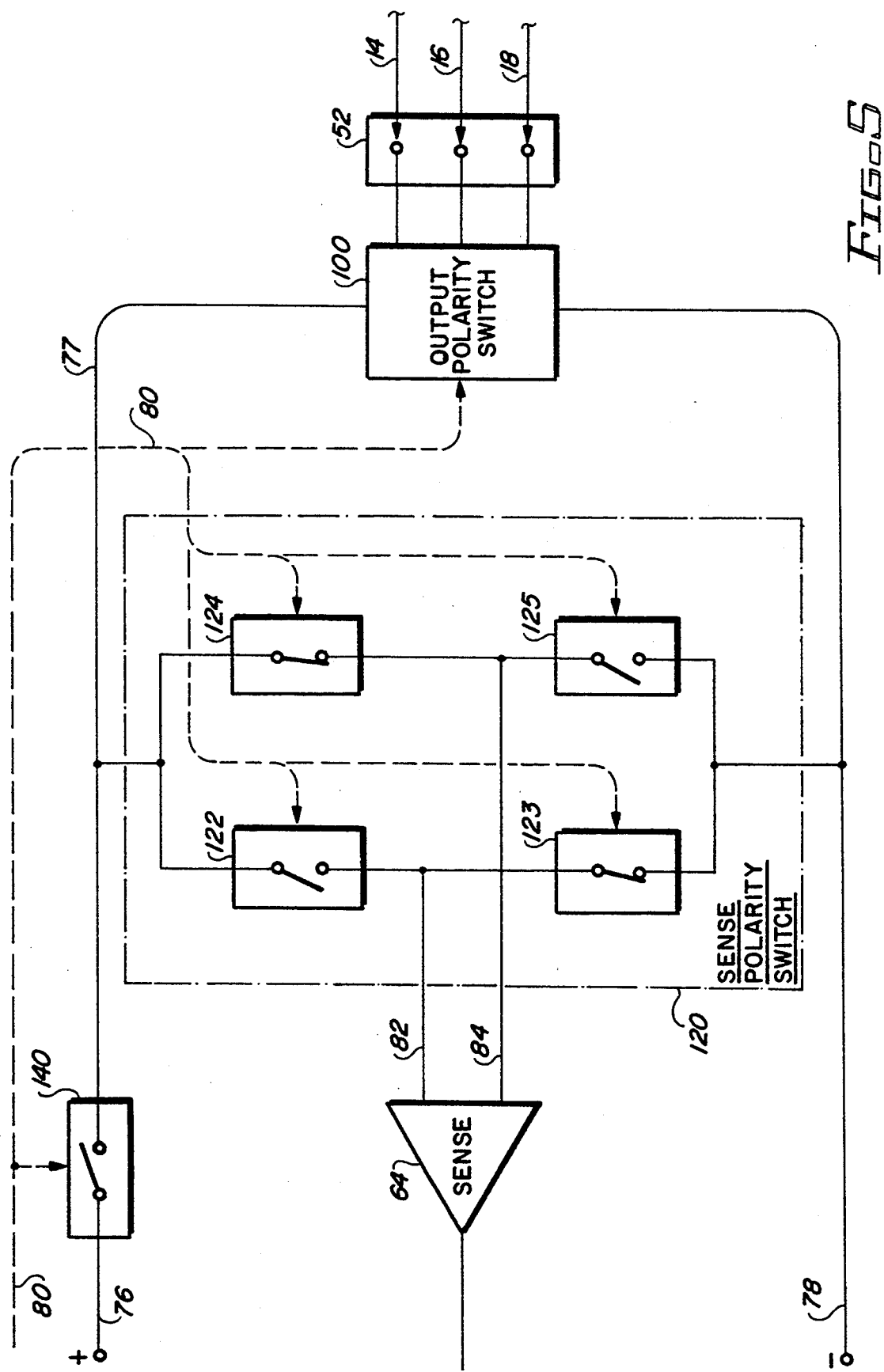
FIG. 5 is a schematic functional diagram of a sense polarity switch that may be included, in some embodiments, of the programmable output connector of FIG. 4.

Each of the individual switches of each switch pair within the output polarity switch 100 is controlled by an appropriate control parameter obtained from the control bus 80. The control bus 80 is depicted in FIG. 5 (as well as in FIG. 4) as a dotted line. Assuming all three output terminals 70, 72 and 74 are to be configured, the following example illustrates a simple method in which a three-bit polarity word may be used to define the programmed polarity of the output terminals. For example, a polarity word "100" may be used to define that the first output terminal 70 is to be positive (logic bit "1"), the second output terminal 72 is to be negative (logic bit "0"), and the third output terminal 74 is to also be negative (logic bit "0"). Other possible combinations for the three output connectors include: "101," "110," "010," "011" and "001." There are thus six possible polarity configurations that may be programmed assuming that all three output connectors are never programmed to the same polarity ("111" and "000").

Figures 6, 7:
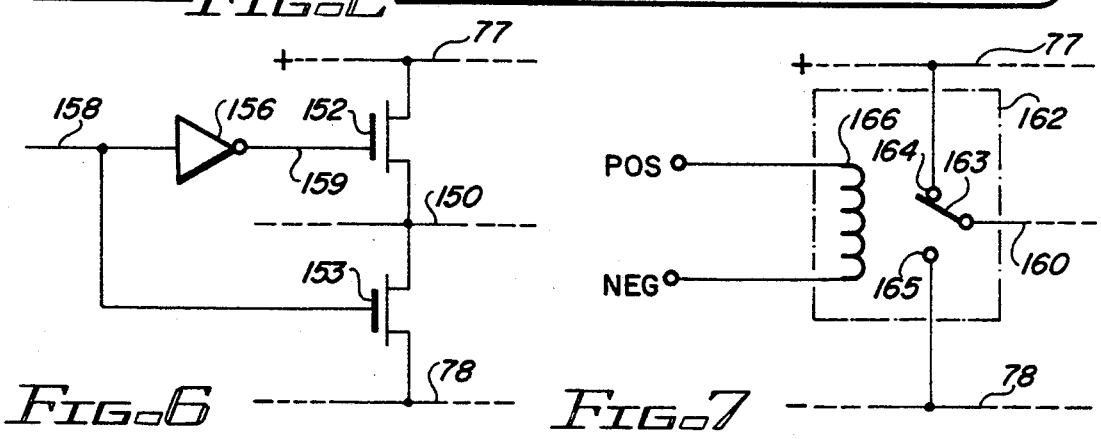
FIG. 6 shows a simplified electrical schematic diagram of a solid-state output switch pair that may be used by the present invention.
FIG. 7 similarly shows a simplified electrical schematic diagram of a latch relay output switch that may be used by the present invention.

As shown in FIG. 6, the same control parameter used to control the first switch of a given switch pair could be modified (e.g., by inverting the signal) so as to control the second switch of the switch pair, thereby assuring that only one switch of each switch pair is closed at any given time. As illustrated in FIG. 7, the switch network 54 may include a "single-pole, double-throw" switch, so that a single control parameter operates both switch functions in the desired manner.

Alternately, it may be desirable for one or more electrodes to be programmed to an OFF state. For example, when three electrodes are implanted, it may be discovered that a particular two electrodes are more efficient (i.e., have a lower threshold) than using all three. This becomes an even more valuable feature when four, five or six electrodes are employed. Suffice it to say, that it is well known in the art to design hardware and/or software which can independently program each electrode to one of a positive, negative or OFF state. Furthermore, it is well known in the art to design hardware and/or software which can ensure that at least one electrode is connected positively and at least one electrode is connected negatively.

It should also be noted that if any of these combinations of electrode polarity are found to be unsafe, then they may be easily locked-out by the external programmer 68 such that the code for the unsafe electrode combination could not be transmitted. One method to ensure safe programming is to have the physician program into the ICD's memory the lead type (e.g., transvenous, epicardial patch, subcutaneous, etc.) and the placement of the lead (e.g., right or left ventricle, atrium, SVC, coronary sinus, etc.). Thus, any attending physician can interrogate the ICD and determine the exact shocking configuration and, if necessary, proceed to evaluate the effectiveness of the electrode polarity and alter it accordingly.

In operation, the physician, after implanting the leads so as to place the electrodes 20, 22 and 24 at a desired cardiac tissue location, connects the proximal ends of such leads to the ICD by inserting such proximal ends into the connector block 52. The physician then determines which of the multiplicity of output terminals should be positive and which should be negative. Such determination will initially be made in large part based on the location of the respective electrodes that are coupled to such output terminals. However, such determination may also be based on experience, intuition or may be arbitrary, at least initially.

For example, assume that the physician determines that electrodes 20 and 22 should be negative, and electrode 24 should be positive. The external programmer 68, or equivalent programming device, is then used to program output terminals 70 and 72 to be negative, and output terminal 74 to be positive. (As a practical matter, if two of three output terminals are programmed to be one polarity, the other output terminal could automatically be programmed to be of the opposite polarity.) Such programming is achieved by sending to the sensing and control logic 62 a set of control parameters. The sensing and control logic responds to the receipt of the control parameters by saving it in an appropriate form in a memory or register of the sensing and control logic, and generating therefrom the appropriate control signals needed to control the switch pairs of the output polarity switch so as to cause the programmed polarity of the output terminals.

With the output terminals of the ICD configured as programmed, the ICD is allowed to function in its normal manner. Thus, if a cardiac arrhythmia or other cardiac condition is sensed warranting a shocking pulse, the output capacitor 56 is charged, and at the appropriate time the discharge switch is closed, thereby delivering the shocking pulse through the output terminals to the electrodes in accordance with the programmed polarity.

For some applications, it is noted that the switch pairs used within the output polarity switch 100 may also function as the discharge switch 140, thereby obviating the need for a separate discharge switch 140. Thus, for example, all of the individual switches may be held in an "open" state until such time as a determination is made that a shocking pulse is needed. (This assumes that sensing can occur through some means other than the output terminals, e.g., through a separate sensing lead 38 (FIG. 2)). When the shocking pulse is needed, and when the output capacitor 56 has been charged to the appropriate level, then one switch of each switch pair is closed in order to discharge the switch through the output terminals in accordance with the programmed polarity. For example, assuming a "110" desired polarity as described above, all of the switches of the output polarity switch 100 would be maintained in an "open" state until the shocking pulse was to be delivered, at which time the switches 103, 104 and 106 would be simultaneously closed.

For some embodiments of the invention, a sense polarity switch 120 may also be included within the switch network 54. The details of one embodiment of a sense polarity switch 120 are shown in FIG. 5. As seen in FIG. 5, the sense polarity switch 120 includes two switch pairs 122–123 and 124–125. Each switch pair is used to connect a selected one of the switched bus 77 or the negative output bus 78 to one of the two inputs 82 or 84 of the sense amplifier 64. That is, switch 122 of the switch pair 122-123 connects the switched bus 77 to the sense line 82, while switch 123 of this same switch pair connects the negative output bus 78 to the sense line 82. Similarly, switch 124 of the switch pair 124-125 connects the switched bus 77 to the sense line 84, while switch 125 of this same switch pair connects the negative output bus 78 to the sense line 84. As with the switch pairs of the output polarity switch 100, the switch pairs 122-123 and 124-125 are controlled, or otherwise configured, so that only one switch of each switch pair may be closed at any given time. Thus, it is not possible to connect both the switched bus 77 and the negative output bus 78 to the same sense line 82 or 84 at the same time. However, by setting the appropriate control parameters available on the control bus 80, it is possible to programmably switch which output bus—the switched bus 77 or the negative bus 78—is connected to a given sense line 82 or 84. Such versatility affords the physician the ability to occasionally switch the polarity of the sensing signals being applied to the sense amplifier 64 in order to determine if improved sensing capabilities might result.

In FIG. 6, a simplified electrical schematic diagram of a solid-state output switch pair is shown. Such solid-state switch pair may be used by the present invention in the output polarity switch 100 or in the sense polarity switch 120. The switch pair comprises a first MOSFET-type transistor 152 having its source terminal connected to the switched (positive) voltage bus 77 and its drain terminal connected to its respective output terminal 150. (Note: as used herein, a MOSFET-type transistor may comprise any type of solid-state transistor switch that provides a high or low impedance as controlled by a suitable control signal.) A second MOSFET-type transistor 153 has its source terminal connected to the output terminal 150, and its drain terminal connected to the negative output bus 78. The gate of the first MOSFET 152 is connected to the output of an inverter gate 156, while the gate of the second MOSFET 153 is connected to the input of the gate 156, which input comprises a control bit 158 of an appropriate polarity word. When the bit is high (a digital "1"), it causes the MOSFET to assume a low resistance state (switch "closed"); and when the bit is low (a digital "0"), it causes the MOSFET to assume a high resistance state (switch "open"); or vice versa (depending upon the type of MOSFET device used). The gate signal applied to the MOSFET 152 will always be opposite to the gate signal applied to the MOSFET 153 because of the inverter gate 156. Hence, MOSFET 152 will always be "closed" when MOSFET 153 is "open"; and MOSFET 152 will always be "open" when MOSFET 153 is "closed."

Due to the high currents that may be involved in a typical shocking pulse, which high currents must pass through the appropriate closed switch of the switch pair, a MOSFET or other semiconductor switch must be used that is capable of handling such large currents. Solid-state switching devices capable of handling large currents are commercially available from numerous sources and their manner of use is known to those of skill in the art. Any of these solid-state switches could be used and controlled as is shown or suggested in FIG. 6. The MOSFET switch, for example, may be used in turn to switchably control another type of solid-state switch (such as a bipolar transistor) having much higher current carrying capacity.

Further, it is noted that whenever solid-state switches are used in an implantable medical device, particularly as an output switch of the medical device, some sort of protection means may be needed in order to protect the switch from transient currents or voltages that could cause the switch to malfunction or be damaged. One type of protection circuit that may be used to protect the solid-state output switches of an implantable medical device is disclosed in U.S. Pat. No. 4,739,437 (Morgan), incorporated herein by reference.

In FIG. 7, a simplified electrical schematic diagram of a latch relay output switch is shown. Such latch relay switch may be used by the present invention in the output polarity switch 100 or the sense polarity switch 120. A latch-relay output switch may be particularly advantageous for use in the output polarity switch 100 because latch relays are readily available commercially at a nominal cost, can readily handle large currents, are very reliable, and the number of times that the latch relays would need to be switched (assuming the use of a discharge switch 140), would be quite small.

As seen in FIG. 7, a latch relay output switch 162 includes an armature 163 that toggles between a first terminal 164 or a second terminal 165. The switched (positive) bus 77 is connected to the first terminal 164. The negative voltage bus 78 is connected to the second terminal 165. The armature 163 is connected to the applicable output terminal 160. An appropriate coil 166, or equivalent, when energized with an appropriate momentary pulse of the proper polarity causes the armature 163 to connect with either the first terminal 164 or the second terminal 165. Thus, the polarity control signal (bit of the polarity word) is appropriately converted to control pulses that cause the relay 162 to connect the output terminal 160 to either the switched (positive) bus 77 or the negative output bus 78. As the armature 63 can only be in one latched position at a time, there is no danger that the switched (positive) bus 77 could be shorted to the negative voltage bus (78). In this manner, the latch relay 162 performs the same function as the switch pairs previously described.

As described above, it is thus seen that the invention provides an ICD that can be implanted in a patient and coupled to a multiplicity of defibrillation leads and electrodes, while still preserving the ability to change the polarity of the electrodes after implantation.

As further described above, it is seen that the invention provides an ICD that can be noninvasively programmed as required in order to selectively alter its output polarity configuration.

Moreover, it is seen that the invention provides a programmable output connector for use with an implantable medical device, such as an ICD, that selectively configures the output terminals of the device to a desired polarity. Advantageously, such programmable output connector allows a multiplicity of defibrillation leads and electrodes to be connected to the ICD in accordance with a programmed polarity, without having to physically alter the placement of the defibrillation leads.

As further evident from the above description, the invention provides a method of programmably altering the polarity of a multiplicity of output terminals of an ICD.

While the invention herein disclosed has been described by means of specific embodiments and applications thereof, numerous modifications and variations could be made thereto by those skilled in the art without departing from the scope of the invention set forth in the claims.

What is claimed is:

1. An implantable cardioverter defibrillator (ICD) comprising:

at least three output terminals which are adapted to allow a multiplicity of defibrillation lead electrical connectors to be detachably electrically connected thereto;

a positive output bus;

a negative output bus;

a switch network connected to said at least three output terminals, said positive output bus, and said negative output bus, for selectively connecting each of said at least three output terminals to a selected one of said positive output bus and said negative output bus;

an output circuit, connected to said positive output bus and said negative output bus, for developing and storing an electrical charge and providing such stored charge to said positive and negative output buses;

sensing means for sensing cardiac activity;

control means coupled to said switch network for controlling which of said at least three output terminals are connected to which of said positive and negative output buses, said control means also operatively controlling said output circuit and said sensing means to determine when a shocking pulse is needed and for controlling the output circuit and switch network so as to initiate discharge of a shocking pulse through said switch network to said at least three output terminals when a shocking pulse is needed; and telemetry means for noninvasively programming said control means to select which of said at least three output terminals will be connected by said switch network to which of said positive and negative output buses.

2. The ICD, as set forth in claim 1, wherein said switch network comprises:

at least three programmable switch pairs, each of said at least three switch pairs being respectively connected to one of said at least three output terminals, a first switch of each switch pair being operable to switchably connect the respective output terminal to said positive output bus, and a second switch of each switch pair being operable to switchably connect the respective output terminal to said negative output bus; and means for ensuring that when a selected one of said first and second switches of each switch pair electrically connects the respective output terminal to a selected one of said positive and negative output buses, the other of said first and second switches of the switch pair electrically disconnects the respective output terminal from the other of said positive and negative output buses, whereby the respective output terminal is electrically connected to only the selected one of said positive and negative output buses;

whereby each of said at least three output terminals may be programmably configured either as a positive output terminal coupled to said positive output bus, or as a negative output terminal coupled to said negative output bus.

3. The ICD, as set forth in claim 2, wherein said switch network further comprises discharge switch means for electrically connecting said output circuit in series between said positive and negative output buses for a controlled time period.

4. The ICD, as set forth in claim 1, wherein said switch network comprises:

at least three programmable switching means each respectively connected to one of said at least three output terminals, each switching means being for switchably connecting the respective output terminal to one of said positive output bus and said negative output bus, or to neither said positive output bus or said negative output bus but rather being in an open state;

means for ensuring that each of said switching means electrically connects the respective output terminal to not more than a selected one of said positive output bus and said negative output bus; and means for ensuring that at least one of said at least three output terminals is connected to said positive output bus and at least one of said at least three output terminals is connected to said negative output bus.

5. The ICD, as set forth in claim 4, wherein the ICD is adapted to be coupled to first, second, and third implantable lead electrodes, with the first, second, and third lead electrodes each being characterizable as one of a plurality of lead types, and with the first, second, and third lead electrodes each being characterizable as having a particular placement position, the ICD further comprising:

memory means, located within the ICD, for storing information characterizing the lead type and placement position of each of the first, second, and third lead electrodes;

means for programming said memory means with information characterizing the lead type and placement position of each of the first, second, and third lead electrodes; and means for preventing said control means from implementing a configuration in which said multiplicity of output terminals are connected to said positive and negative output buses in a manner which results in an unsafe electrode polarity in view of the information characterizing the lead type and placement position.

6. An implantable cardioverter-defibrillator (ICD) having a programmable polarity output connector, the ICD comprising:

a charge supply means for holding a prescribed charge in anticipation of transferring the charge from the charge supply means to cardiac tissue of a patient, the charge supply means having a positive supply terminal and a negative supply terminal;

at least a first, a second, and a third output terminal; and programmable switching means for programmably switching a selected one of said first, second, and third output terminals to said positive supply terminal, and a selected other of said first, second, and third output terminals to said negative supply terminal;

whereby said first, second, and third output terminals may be programmed to assume a desired polarity with respect to said positive and negative supply terminals, with at least one of said first, second, and third output terminals being coupled to said positive supply terminal, and with at least another of said first, second, and third output terminals being coupled to said negative supply terminal; whereby said charge supply means may be discharged through selected ones of said first, second, and third output terminals while said selected ones of said first, second, and third output terminals assume a selected polarity relative to said positive and negative supply terminals.

7. The ICD, as set forth in claim 6, further comprising:
a positive output bus and a negative output bus, said positive output bus being coupled to said positive supply terminal, and said negative output bus being coupled to said negative supply terminal;
a discharge switch that switches one of said positive and negative output buses to the respective positive or negative supply terminal; and
wherein said programmable switching means is coupled to said positive and negative output buses and switches said selected one of said first, second or third output terminals to said positive supply terminal through said positive output bus, and switches said selected other of said first, second or third output terminals to said negative supply terminal through said negative output bus;
whereby said charge supply means may be selectively discharged through selected ones of said first, second, and third output terminals in accordance with the polarity selected by said programmable switching means when said discharge switch is closed.

8. The ICD, as set forth in claim 7, wherein said programmable switching means comprises an output polarity switch network made up of first, second, and third switch pairs, each of said first second, and third switch pairs, comprising:
a positive switch for selectively connecting a respective output terminal to said positive output bus, and a negative switch for selectively connecting the respective output terminal to said negative output bus; and
control means for preventing said positive switch from connecting the respective output terminal to said positive output bus at the same time that said negative switch is connecting the respective output terminal to said negative output bus, whereby said positive and negative output buses are prevented from being electrically shorted together through the switch pair.

9. The ICD, as set forth in claim 8, wherein:
said positive switch of each switch pair comprises a solid-state switch that is closed or in a low resistance state in response to a first control signal assuming a first condition, and is open or in a high resistance state in response to said first control signal assuming a second condition;
said negative switch of each switch pair comprises a solid-state switch that is closed or in a low resistance state in response to a second control signal assuming a first condition, and is open or in a high resistance state in response to said second control signal assuming a second condition; and
said control means comprises circuit means for generating said first and second control signals, said first and second control signals being related such that said first control signal assumes said first condition whenever said second control signal assumes said second condition, and said first control signal assumes said second condition whenever said second control signal assumes said first condition, whereby only one of said positive switch and said negative switch is closed at any given time.

10. The ICD, as set forth in claim 8, wherein:
said positive switch of each switch pair comprises a first latch relay, and said negative switch of each switch pair comprises a second latch relay, said first and second latch relays being configured so that said first latch relay is closed when said second latch relay is open, and said first latch relay is open when said second latch relay is closed.

11. The ICD, as set forth in claim 8, wherein the ICD is adapted to be coupled to first, second, and third implantable lead electrodes, with the first, second, and third lead electrodes each being characterizable as one of a plurality of lead types, and with the first, second, and third lead electrodes each being characterizable as having a particular placement position, the ICD further comprising:
memory means, located within the ICD, for storing information characterizing the lead type and placement position of each of the first, second, and third lead electrodes;
means for programming said memory means with information characterizing the lead type and placement position of each of said first, second, and third lead electrodes; and
means for preventing said control means from implementing a configuration in which said first, second, and third output terminals are connected to said positive and negative output buses in a manner which results in an illegal electrode polarity in view of the information characterizing the lead type and placement position.

12. The ICD, as set forth in claim 7, further comprising a first sensing input terminal and a second sensing input terminal and wherein said programmable switching means comprises:
a programmable sense polarity switch network connected to said first sensing input terminal, said second sensing input terminal, and said first, second, and third output terminals for programmably switching a selected one of said first, second, and third output terminals to said first sensing input terminal, and a selected other of said first, second, and third output terminals to said second sensing input terminal.

13. The ICD, as set forth in claim 12, wherein said programmable sense polarity switch network comprises:
first and second sensing switch pairs, said first sensing switch pair comprising a positive sensing switch for selectively connecting said positive output bus to a first sensing input terminal, and a negative sensing switch for selectively connecting said negative output bus to said first sensing input terminal, and said second sensing switch pair comprising a positive sensing switch for selectively connecting said positive output bus to a second sensing input terminal, and a negative sensing switch for selectively connecting said negative output bus to said second sensing input terminal;
wherein both said first and second sensing switch pairs comprise means for connecting only one of said positive output bus and said negative output bus to a respective one of said first and second sensing input terminals at any given time;
whereby said first and second sensing input terminals may be selectively connected to said positive output bus and said negative output bus, said positive and negative output buses are connected by said output polarity switch network to a desired combination of said first, second and third output terminals.

14. A programmable polarity output apparatus for use with an implantable medical device, the implantable medical device having a first sensing input terminal, a second sensing input terminal, a positive output bus and a negative output bus, the programmable polarity output apparatus comprising:

first, second, and third output terminals; and programmable switching means for programmably switching a selected one of said first, second, and third output terminals to the positive output bus, and a selected other one of said first, second, and third output terminals to the negative output bus;

whereby said first, second, and third output terminals may be programmed to assume a desired polarity with respect to the positive and negative output buses, with at least one of said first, second, and third output terminals being switched to the positive output bus, and with at least another one of the first, second or third output terminals being switched to the negative output bus;

and whereby the positive and negative output buses may contact body tissue through selected ones of said first, second, and third output terminals in accordance with a programmed polarity, the programmed polarity being determined by which one or ones of said first, second, and third output terminals are switched to the positive output bus, and which one or ones of said first, second, and third output terminals are switched to the negative output bus.

15. The programmable output polarity apparatus for use with an implantable medical device, as set forth in claim 14, wherein said programmable switching means comprises an output polarity switch network made up of first, second, and third switch pairs, each of said first, second, and third switch pairs comprising:

a positive switch for selectively connecting a respective output terminal to the positive output bus, and a negative switch for selectively connecting the respective output terminal to the negative output bus; and control means for preventing said positive switch from connecting the respective output terminal to the positive output bus at the same time that said negative switch is connecting the respective output terminal to the negative output bus, whereby the positive and negative output buses are prevented from being electrically shorted together through the switch pair.

16. The programmable polarity output apparatus for use with an implantable medical device, as set forth in claim 15, wherein:

said positive and negative switches of each switch pair each comprise a solid-state switch that is closed or in a low resistance state in response to application of a control signal assuming a first condition, and is open or in a high resistance state in response to application of a control signal assuming a second condition; and said control means comprises circuit means for generating first and second control signals, said first control signal being applied to said positive switch, and said second control signal being applied to said negative switch, said first and second control signals being related such that said first control signal assumes said first condition whenever said second control signal assumes said second condition, and said first control signal assumes said second condition whenever said second control signal assumes said first condition, whereby only one of said positive and negative switches is closed at any given time.

17. The programmable polarity output apparatus for use with an implantable medical device, as set forth in claim 15, wherein said positive switch of each switch pair comprises a first latch relay, and said negative switch of each switch pair comprises a second latch relay, said first and second latch relays being configured so that said first latch relay is closed when said second latch relay is open, and said first latch relay is open when said second latch relay is closed.

18. The programmable polarity output apparatus for use with an implantable medical device, as set forth in claim 15, wherein said programmable switching means further comprises:

a sense polarity switch network, connected to said first sensing input terminal, said second sensing input terminal, said positive output bus, and said negative output bus, comprising first and second sensing switch pairs, said first sensing switch pair comprising a positive sensing switch for selectively connecting the positive output bus to said first sensing input terminal, and a negative sensing switch for selectively connecting the negative output bus to said first sensing input terminal, and said second sensing switch pair likewise comprising a positive sensing switch for selectively connecting the positive output bus to said second sensing input terminal, and a negative sensing switch for selectively connecting the negative output bus to said second sensing input terminal, both said first and second sensing switch pairs further comprising means for connecting only one of the positive output bus and the negative output bus to a respective one of said first and second sensing input terminals at any given time;

whereby said first and second sensing input terminals may be selectively connected to a desired combination of said first, second, and third output terminals.

19. The programmable polarity output apparatus for use with an implantable medical device, as set forth in claim 18, said implantable medical device further housing discharge circuitry, and wherein said output polarity switch network further comprises a discharge switch that switches one of the positive or negative output buses to said discharge circuitry.

20. A method of programmably altering the polarity of at least three output terminals of an implantable cardioverter-defibrillator (ICD), the method comprising the steps of:

(a) connecting each of the at least three output terminals to a corresponding one of at least three switch pairs, each of said at least three switch pairs comprising a positive switch that switchably connects the corresponding output terminal to a positive voltage bus, and a negative switch that switchably connects the corresponding output terminal to a negative voltage bus;

(b) controlling each of said switch pairs so that when said positive switch of a given switch pair connects its corresponding output terminal to said positive voltage bus, said negative switch of said given switch pair disconnects the corresponding output terminal from said negative voltage bus, and so that when said negative switch of said given switch pair connects the corresponding output terminal to said negative voltage bus, said positive switch of said given switch pair disconnects the corresponding output terminal from said positive voltage bus, whereby it is not possible to short said positive voltage bus to said negative voltage bus through said given switch pair;

(c) further controlling said switch pairs so that at least the positive switch of one switch pair connects its corresponding output terminal to said positive voltage bus at the same time that the negative switch of another switch pair connects its corresponding output terminal to said negative voltage bus; and (d) programmably setting said positive and negative switches of each of said at least three switch pairs so that the corresponding output terminal is connected to one of said positive or negative voltage buses, thereby configuring the output terminals to assume a desired polarity relative to each other and said positive and negative voltage buses, with at least one of the at least three output terminals being switched to said positive voltage bus, and another of the at least three output terminals being switched to said negative voltage bus.

21. The method, as set forth in claim 20, wherein said ICD includes an output circuit, and wherein said method further includes the step of:

connecting a discharge switch between the output circuit and said positive and negative voltage buses, and closing said discharge switch whenever an output voltage stimulus generated by the output circuit is to be delivered to the at least three output terminals, whereby said output voltage stimulus appears across the at least three output terminals with a polarity set in step (d).

22. The method, as set forth in claim 21, further comprising sensing any electrical signals that may be present on said positive and negative voltage buses at a time when said discharge switch is open, and thus at a time when the output circuit is disconnected from said positive and negative voltage buses.

* * * * *